United States Patent
De La Mettrie et al.

(10) Patent No.: US 6,840,966 B1
(45) Date of Patent: Jan. 11, 2005

(54) COMPOSITION FOR THE OXIDATION DYEING OF KERATIN FIBERS AND DYEING PROCESS USING THIS COMPOSITION

(75) Inventors: Roland De La Mettrie, Le Vesinet (FR); Jean Cotteret, Verneuil-sur-Seine (FR); Arnaud De Labbey, Aulnay sous Bois (FR); Mireille Maubru, Chatou (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/645,881

(22) Filed: Aug. 22, 2003

Related U.S. Application Data

(63) Continuation of application No. 09/319,165, filed on Feb. 15, 2001, now abandoned.

(30) Foreign Application Priority Data

Oct. 3, 1997 (FR) .......................................... 97 12352

(51) Int. Cl.$^7$ ................................................. A61K 7/13
(52) U.S. Cl. ....................... 8/405; 8/406; 8/407; 8/408; 8/409; 8/410; 8/411; 8/412; 8/421
(58) Field of Search ........................... 8/405, 406, 408, 8/409, 410, 411, 412, 421

(56) References Cited

U.S. PATENT DOCUMENTS

| | | | | |
|---|---|---|---|---|
| 4,065,255 A | * | 12/1977 | Andrillon et al. | 8/412 |
| 4,228,259 A | * | 10/1980 | Kalopissis et al. | 525/435 |
| 4,323,360 A | * | 4/1982 | Bugaut et al. | 8/407 |
| 4,985,042 A | * | 1/1991 | Bugaut et al. | 8/421 |
| 5,849,041 A | * | 12/1998 | Kunz et al. | 8/408 |

* cited by examiner

*Primary Examiner*—Yogendra N. Gupta
*Assistant Examiner*—Eisa Elhilo
(74) *Attorney, Agent, or Firm*—Finnegan, Henderson, Farabow, Garrett & Dunner, L.L.P.

(57) ABSTRACT

The invention relates to a ready-to-use composition for the oxidation dyeing of keratin fibres, and in particular human keratin fibres such as the hair, comprising, in a medium which is suitable for dyeing, para-phenylenediamine as first oxidation base, at least one para-aminophenol as second oxidation base, 2-methyl-5-N-(β-hydroxyethyl) aminophenol as coupler and at least one enzyme of 2-electron oxidoreductase type in the presence of at least one donor for the said enzyme, and to the dyeing process using this composition.

41 Claims, No Drawings

COMPOSITION FOR THE OXIDATION DYEING OF KERATIN FIBERS AND DYEING PROCESS USING THIS COMPOSITION

This is a continuation of application Ser. No. 09/319,165, filed Feb. 15, 2001 now abandoned, which claims priority under 35 U.S.C. § 365 to PCT App. No. FR98/02077, filed Sep. 28, 1998, which claims priority to French App. No. FR 97/12352, filed Oct. 3, 1997, all of which are hereby incorporated by reference.

The invention relates to a composition for the oxidation dyeing of keratin fibres, and in particular human keratin fibres such as the hair, comprising, in a medium which is suitable for dyeing, para-phenylenediamine as first oxidation base, at least one para-aminophenol as second oxidation base, 2-methyl-5-N-(β-hydroxyethyl)aminophenol as coupler and at least one enzyme of 2-electron oxidoreductase type in the presence of at least one donor for the said enzyme, and to the dyeing process using this composition.

It is known to dye keratin fibres, and in particular human hair, with dye compositions containing oxidation dye precursors, in particular ortho- or para-phenylenediamines, ortho- or para-aminophenols and heterocyclic bases, which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used as oxidation bases and couplers allows a wide range of colours to be obtained.

The so-called "permanent" coloration obtained by means of these oxidation dyes must moreover satisfy a certain number of requirements. Thus, it must have no toxicological drawbacks, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible colour differences along the same length of keratin fibre, which may in fact be differently sensitized (i.e. damaged) between its tip and its root.

The oxidation dyeing of keratin fibres is generally carried out in alkaline medium, in the presence of hydrogen peroxide. However, the use of alkaline media in the presence of hydrogen peroxide have the drawback of causing appreciable degradation of the fibres, as well as considerable bleaching of the keratin fibres, which is not always desirable.

The oxidation dyeing of keratin fibres can also be carried out using oxidizing systems other than hydrogen peroxide, such as enzymatic systems. Thus, it has already been proposed to dye keratin fibres, in particular in patent application EP-A-0,310,675, with compositions comprising an oxidation base and optionally a coupler, in combination with enzymes such as pyranose oxidase, glucose oxidase or uricase, in the presence of a donor for the said enzymes. Although being used under conditions which do not result in a degradation of the keratin fibres which is comparable to that caused by the dyes used in the presence of hydrogen peroxide, these dyeing processes nevertheless lead to colorations which are not entirely satisfactory, in particular as regards their intensity and resistance to the various attacking factors to which the hair may be subjected.

The Applicant has now discovered that it is possible to obtain new dyes, which are capable of leading to intense colorations, without giving rise to any significant degradation of the keratin fibres, and which are relatively unselective and show good resistance to the various attacking factors to which the hair may be subjected, by combining para-phenylenediamine as first oxidation base, at least one para-aminophenol as second oxidation base, 2-methyl-5-N-(β-hydroxyethyl)aminophenol as coupler and at least one enzyme of 2-electron oxidoreductase type in the presence of at least one donor for the said enzyme.

This discovery forms the basis of the present invention.

A first subject of the invention is thus a ready-to-use composition for the oxidation dyeing of keratin fibres, and in particular human keratin fibres such as the hair, characterized in that it comprises, in a medium which is suitable for dyeing:

para-phenylenediamine and/or at least one of the addition salts thereof with an acid, as first oxidation base, at least one second oxidation base chosen from para-aminophenols, 2-methyl-5-N-(β-hydroxyethyl)aminophenol and/or at least one of the addition salts thereof with an acid, as coupler, at least one enzyme of 2-electron oxidoreductase type, and at least one donor for the said enzyme.

The ready-to-use dye composition in accordance with the invention leads to intense relatively unselective colorations with excellent properties of resistance both to atmospheric agents such as light and bad weather and to perspiration and the various treatments to which the hair may be subjected (washing, permanent-waving).

A subject of the invention is also a process for the oxidation dyeing of keratin fibres using this ready-to-use dye composition.

The 2-electron oxidoreductase(s) used in the ready-to-use dye composition in accordance with the invention can be chosen in particular from pyranose oxidases, glucose oxidases, glycerol oxidases, lactate oxidases, pyruvate oxidases and uricases.

According to the invention, the 2-electron oxidoreductase is preferably chosen from uricases of animal, microbiological or biotechnological origin.

By way of example, mention may be made of uricase extracted from boar liver, uricase from Arthrobacter globiformis, as well as uricase from Aspergillus flavus.

The 2-electron oxidoreductase(s) can be used in pure crystalline form or in a form diluted in a diluent which is inert with respect to the said 2-electron oxidoreductase.

The 2-electron oxidoreductase(s) in accordance with the invention preferably represent(s) from 0.01 to 20% by weight approximately relative to the total weight of the ready-to-use dye composition, and even more preferably from 0.1 to 5% by weight approximately relative to this weight.

According to the invention, the term donor is understood to refer to the various substrates involved in the functioning of the said 2-electron oxidoreductase(s).

The nature of the donor (or substrate) for the said enzyme varies depending on the nature of the 2-electron oxidoreductase used. For example, as donors for the pyranose oxidases, mention may be made of D-glucose, L-sorbose and D-xylose; as a donor for the glucose oxidases, mention may be made of D-glucose; as donors for the glycerol oxidases, mention may be made of glycerol and dihydroxyacetone; as donors for the lactate oxidases, mention may be made of lactic acid and its salts; as donors for the pyruvate oxidases, mention may be made of pyruvic acid and its salts; and lastly, as donors for the uricases, mention may be made of uric acid and its salts.

The donor(s) (or substrate(s)) used in accordance with the invention preferably represent(s) from 0.01 to 20% by weight approximately relative to the total weight of the ready-to-use dye composition in accordance with the invention, and even more preferably from 0.1 to 5% by approximately relative to this weight.

Among the para-aminophenols which can be used as oxidation bases in the dye compositions in accordance with the invention, mention may be made in particular of the compounds corresponding to formula (I) below, and the addition salts thereof with an acid:

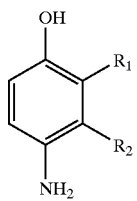

(I)

in which:
R$_1$ represents a hydrogen or halogen atom or a C$_1$–C$_4$ alkyl, C$_1$–C$_4$ monohydroxyalkyl, (C$_1$–C$_4$)alkoxy (C$_1$–C$_4$)alkyl, C$_1$–C$_4$ aminoalkyl or hydroxy(C$_1$–C$_4$) alkylamino(C$_1$–C$_4$)alkyl radical, R$_2$ represents a hydrogen or halogen atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy-(C$_1$–C$_4$)alkyl radical, it being understood that at least one of the radicals R$_1$ or R$_2$ represents a hydrogen atom.

Among the para-aminophenols of formula (I) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

The para-phenylenediamine and/or the addition salt(s) thereof with an acid which can be used as first oxidation base preferably represent(s) from 0.0005 to 12% by weight approximately relative to the total weight of the ready-to-use dye composition in accordance with the invention, and even more preferably from 0.005 to 6% by weight approximately relative to this weight.

The para-aminophenol(s) which can be used as second oxidation base preferably represent(s) from 0.0005 to 12% by weight approximately relative to the total weight of the ready-to-use dye composition in accordance with the invention, and even more preferably from 0.005 to 6% by weight approximately relative to this weight.

The 2-methyl-5-N-(β-hydroxyethyl)aminophenol and/or the addition salt(s) thereof with an acid which can be used as coupler preferably represent(s) from 0.0001 to 5% by weight approximately relative to the total weight of the ready-to-use dye composition, and even more preferably from 0.005 to 3% by weight approximately relative to this weight.

The ready-to-use dye composition in accordance with the invention can also contain one or more additional couplers other than 2-methyl-5-N-(β-hydroxyethyl)aminophenol and the addition salts thereof with an acid and/or one or more direct dyes, in particular in order to modify the shades or to enrich is them with glints.

Among the couplers which can be present additionally in the ready-to-use dye composition in accordance with the invention, mention may be made in particular of meta-phenylenediamines, meta-aminophenols other than 2-methyl-5-N-(β-hydroxyethyl)aminophenol and the addition salts thereof with an acid, meta-diphenols and heterocyclic couplers, and the addition salts thereof with an acid.

When they are present, these additional couplers preferably represent from 0.0001 to 10% by weight approximately relative to the total weight of the ready-to-use dye composition, and even more preferably from 0.005 to 5% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium which is suitable for dyeing (or support) for the ready-to-use dye composition in accordance with the invention generally consists of water or a mixture of water and at least one organic solvent to dissolve the compounds which would not be sufficiently soluble in water. By way of organic solvents, mention may be made, for example, of C$_1$–C$_4$ alkanols, such as ethanol and isopropanol; glycerol; is glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the ready-to-use dye composition, and even more preferably between 5 and 30% by weight approximately.

The pH of the ready-to-use composition in accordance with the invention is chosen such that the enzymatic activity of the 2-electron oxidoreductase is sufficient. It is generally between 5 and 11 approximately, and preferably between 6.5 and 10 approximately. It can be adjusted to the desired value using acidifying or basifying agents usually used for dyeing keratin fibres.

Among the acidifying agents, mention may be made, by way of example, of inorganic or organic acids such as hydrochloric acid, orthophosphoric acid, sulphuric acid, carboxylic acids such as acetic acid, tartaric acid, citric acid or lactic acid, and sulphonic acids.

Among the basifying agents, mention may be made, by way of example, of aqueous ammonia, alkaline carbonates, alkanolamines such as mono-, di- and triethanolamines, 2-methyl-2-aminopropanol and derivatives thereof, sodium hydroxide, potassium hydroxide and the compounds of formula (II) below:

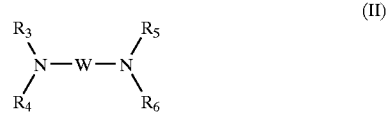

(II)

in which W is a propylene residue optionally substituted with a hydroxyl group or a C$_1$–C$_4$ alkyl radical; R$_3$, R$_4$, R$_5$ and R$_6$, which may be identical or different, represent a hydrogen atom or a C$_1$–C$_4$ alkyl or C$_1$–C$_4$ hydroxyalkyl radical.

The ready-to-use dye composition in accordance with the invention can also contain various adjuvants used conventionally in compositions for the dyeing of the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, enzymes other than the 2-electron oxidoreductases used in accordance with the invention, such as, for example, peroxidases, penetration agents, sequestering agents, fragrances, buffers, dispersing agents, conditioners such as, for example, silicones which may or may not be volatile or modified, film-forming agents, ceramides, preserving agents and opacifiers.

Needless to say, a person skilled in the art will take care to select this or these optional complementary compound(s) such that the advantageous properties intrinsically associated with the ready-to-use dye composition in accordance with the invention are not, or are not substantially, adversely affected by the addition or additions envisaged.

The ready-to-use dye composition in accordance with the invention can be in various forms, such as in the form of liquids, creams or gels, which may be pressurized, or in any other form which is suitable for dyeing keratin fibres, and in particular human hair. In this case the oxidation dyes and the 2-electron oxidoreductase(s) are present in the same ready-to-use composition, and consequently the said composition must be free of gaseous oxygen, so as to avoid any premature oxidation of the oxidation dye(s).

A subject of the invention is also a process for dyeing keratin fibres, and in particular human keratin fibres such as the hair, using the ready-to-use dye composition as defined above.

According to this process, at least one ready-to-use dye composition as defined above is applied to the fibres, for a period which is sufficient to develop the desired coloration, after which the fibres are rinsed, optionally washed with shampoo, rinsed again and dried.

The time required to develop the coloration on the keratin fibres is usually between 3 and 60 minutes and even more precisely between 5 and 40 minutes.

According to one specific embodiment of the invention, the process includes a preliminary step which consists in separately storing, on the one hand, a composition (A) comprising, in a medium which is suitable for dyeing, para-phenylenediamine and/or at least one of the addition salts thereof with an acid, at least one second oxidation base chosen from para-aminophenols, 2-methyl-5-N-(β-hydroxyethyl)aminophenol and/or at least one of the addition salts thereof with an acid as coupler, and, on the other hand, a composition (B) comprising, in a medium which is suitable for dyeing, at least one enzyme of 2-electron oxidoreductase type in the presence of at least one donor for the said enzyme, and then in mixing them together at the time of use, after which this mixture is applied to the keratin fibres.

Another subject of the invention is a multi-compartment dyeing device or "kit" or any other multi-compartment packaging system, a first compartment of which comprises composition (A) as defined above and a second compartment of which comprises composition (B) as defined above. These devices can be equipped with means for delivering the desired mixture onto the hair, such as the devices described in patent FR-2,586,913 in the name of the Applicant.

The examples which follow are intended to illustrate the invention without, however, limiting its scope.

EXAMPLE

Dyeing Example 1

The ready-to-use dye composition below was prepared:

| | |
|---|---|
| para-Phenylenediamine | 0.216 g |
| para-Aminophenol | 0.1 g |
| 2-Methyl-5-N-(β-hydroxyethyl)aminophenol | 0.18 g |
| Uricase from *Arthrobacter globiformis* at 20 International Units (I.U.)/mg, sold by the company Sigma | 1.5 g |
| Uric acid | 1.5 g |
| Ethanol | 20.0 g |
| Hydroxyethylcellulose sold under the name Natrosol 250HR ® by the company Aqualon | 1.0 g |
| ($C_8$–$C_{10}$)Alkylpolyglucoside as an aqueous solution containing 60% active material (A.M.), buffered with ammonium citrate (0.5%), sold under the name Oramix CG 110 ® by the company SEPPIC | 8.0 g |
| Monoethanolamine qs | pH = 9.5 |
| Demineralized water qs | 100.0 g |

The ready-to-use dye composition described above was applied to locks of natural grey hair containing 90% white hairs, for 30 minutes. The hair was then rinsed, washed with a standard shampoo and then dried.

The hair was dyed in a dark mahogany blonde shade.

What is claimed is:

1. A ready-to-use composition for the oxidation dyeing of keratin fibers, comprising:
   at least one first oxidation base chosen from para-phenylenediamines and acid-addition salts thereof,
   at least one second oxidation base chosen from para-aminophenols and acid-addition salts thereof,
   at least one coupler chosen from 2-methyl-5-N-(β-hydroxyethyl)aminophenol and acid-addition salts thereof,
   at least one enzyme chosen from 2-electron oxidoreductases, and
   at least one donor for said at least one enzyme.

2. The composition according to claim 1, wherein said keratin fibers are human keratin fibers.

3. The composition according to claim 2, wherein said human keratin fibers are human hair.

4. The composition according to claim 1, wherein said at least one enzyme is chosen from pyranose oxidases, glucose oxidases, glycerol oxidases, lactate oxidases, pyruvate oxidases and uricases.

5. The composition according to claim 1, wherein said at least one enzyme is chosen from uricases of animal, microbiological and biotechnological origin.

6. The composition according to claim 1, wherein said at least one enzyme is present in an amount ranging from 0.01 to 20% by weight relative to the total weight of said composition.

7. The composition according to claim 6, wherein said at least one enzyme is present in an amount ranging from 0.1 to 5% by weight relative to the total weight of said composition.

8. The composition according to claim 1, wherein said at least one donor is chosen from D-glucose, L-sorbose, D-xylose, glycerol, dihydroxyacetone, lactic acid and its salts; pyruvic acid and its salts; and uric acid and its salts.

9. The composition according to claim 1, wherein said at least one donor is chosen from uric acid and its salts.

10. The composition according to claim 1, wherein said at least one donor is present in an amount ranging from 0.01 to 20% by weight relative to the total weight of said composition.

11. The composition according to claim 10, wherein said at least one donor is present in an amount ranging from 0.1 to 5% by weight relative to the total weight of said composition.

12. The composition according to claim 1, wherein said para-aminophenols are chosen from compounds corresponding to formula (I) below, and acid-addition salts thereof:

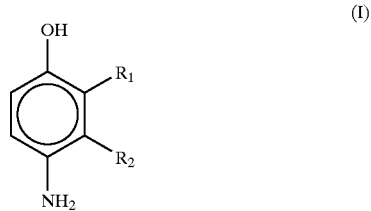

in which:
R$_1$ is chosen from a hydrogen atom, halogen atoms, C$_1$–C$_4$ alkyl radicals, C$_1$–C$_4$ monohydroxyalkyl radicals, (C$_1$–C$_4$)alkoxy(C$_1$–C$_4$)alkyl radicals, C$_1$–C$_4$ aminoalkyl radicals, and hydroxy(C$_1$–C$_4$)alkylamino (C$_1$–C$_4$)alkyl radicals, R$_2$ is chosen from a hydrogen atom, halogen atoms, C$_1$–C$_4$ alkyl radicals, C$_1$–C$_4$ monohydroxyalkyl radicals, C$_2$–C$_4$ polyhydroxyalkyl radicals, C$_1$–C$_4$ aminoalkyl radicals, C$_1$–C$_4$ cyanoalkyl radicals, and (C$_1$–C$_4$)alkoxy-(C$_1$–C$_4$)alkyl radicals, and wherein at least one of said radicals R$_1$ and R$_2$ is a hydrogen atom.

13. The composition according to claim 12, wherein said para-aminophenols of formula (I) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof.

14. The composition according to claim 1, wherein said at least one second oxidation base is present in an amount ranging from 0.0005 to 12% by weight relative to the total weight of said composition.

15. The composition according to claim 14, wherein said at least one second oxidation base is present in an amount ranging from 0.005 to 6% by weight relative to the total weight of said composition.

16. The composition according to claim 1, wherein said at least one first oxidation base is present in an amount ranging from 0.0005 to 12% by weight relative to the total weight of said composition.

17. The composition according to claim 16, wherein said at least one first oxidation base is present in an amount ranging from 0.005 to 6% by weight relative to the total weight of said composition.

18. The composition according to claim 1, wherein said at least one coupler is present in an amount ranging from 0.0001 to 5% by weight relative to the total weight of said composition.

19. The composition according to claim 18, wherein said at least one coupler is present in an amount ranging from 0.005 to 3% by weight relative to the total weight of said composition.

20. The composition according to claim 1, further comprising at least one additional coupler other than 2-methyl-5-N-(β-hydroxyethyl)aminophenol and acid-addition salts thereof.

21. The composition according to claim 20, wherein said at least one additional coupler is chosen from meta-phenylenediamines, meta-aminophenols other than 2-methyl-5-N-(β-hydroxyethyl)aminophenol, meta-diphenols, heterocyclic couplers, and acid-addition salts thereof.

22. The composition according to claim 1, further comprising at least one direct dye.

23. The composition according to claim 1, wherein said acid-addition salts are chosen from hydrochlorides, hydrobromides, sulphates, tartrates, lactates and acetates.

24. The composition according to claim 1, wherein said composition further comprises water or a mixture of water and at least one organic solvent.

25. The composition according to claim 1, wherein said composition has a pH ranging from 5 to 11.

26. The composition according to claim 1, further comprising at least one peroxidase.

27. A ready-to-use composition for the oxidation dyeing of keratin fibers, comprising:
at least one first oxidation base chosen from para-phenylenediamines and acid-addition salts thereof,
at least one second oxidation base chosen from
para-aminophenol compounds chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof,
at least one coupler chosen from 2-methyl-5-N-(β-hydroxyethyl)aminophenol and acid-addition salts thereof,
at least one enzyme chosen from
2-electron oxidoreductases chosen from: pyranose oxidases, glucose oxidases, glycerol oxidases, lactate oxidases, pyruvate oxidases and uricases, and
at least one donor for said at least one enzyme chosen from D-glucose, L-sorbose, D-xylose, glycerol, dihydroxyacetone, lactic acid and its salts; pyruvic acid and its salts; and uric acid and its salts.

28. A ready-to-use composition for the oxidation dyeing of keratin fibers, comprising:
at least one first oxidation base chosen from para-phenylenediamines and acid-addition salts thereof,
at least one second oxidation base chosen from
para-aminophenol compounds chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof,
at least one coupler chosen from 2-methyl-5-N-(β-hydroxyethyl)aminophenol and acid-addition salts thereof,
at least one additional coupler other than 2-methyl-5-N-(β-hydroxyethyl)aminophenol, and acid-addition salts thereof, wherein said at least one additional coupler is chosen from meta-phenylenediamines, meta-aminophenols other than 2-methyl-5-N-(β-hydroxyethyl)aminophenol, meta-aminophenols, heterocyclic couplers, and acid-addition salts thereof, at least one enzyme chosen from
2-electron oxidoreductases chosen from: pyranose oxidases, glucose oxidases, glycerol oxidases, lactate oxidases, pyruvate oxidases and uricases, and at least one donor for said at least one enzyme chosen from D-glucose, L-sorbose, D-xylose, glycerol, dihydroxyacetone, lactic acid and its salts; pyruvic acid and its salts; and uric acid and its salts.

29. A ready-to-use composition for the oxidation dyeing of keratin fibers, comprising:

para-phenylenediamine, para-aminophenol, 2-methyl-5-N-(β-hydroxyethyl)aminophenol, uricase, and uric acid.

30. A process for dyeing keratin fibers, comprising applying a ready-to-use composition for the oxidation dyeing of keratin fibers to said fibers and developing for a period sufficient to achieve a desired coloration, wherein said composition comprises:

at least one first oxidation base chosen from para-phenylenediamines and acid-addition salts thereof, at least one second oxidation base chosen from para-aminophenols and acid-addition salts thereof, at least one coupler chosen from 2-methyl-5-N-(β-hydroxyethyl)aminophenol and acid-addition salts thereof, at least one enzyme chosen from 2-electron oxidoreductases, and at least one donor for said at least one enzyme.

31. A process for dyeing keratin fibers, comprising applying a ready-to-use composition for the oxidation dyeing of keratin fibers to said fibers and developing for a period sufficient to achieve a desired coloration, wherein said composition comprises:

at least one first oxidation base chosen from para-phenylenediamines and acid-addition salts thereof, at least one second oxidation base chosen from
para-aminophenol compounds chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof, at least one coupler chosen from 2-methyl-5-N-(β-hydroxyethyl)aminophenol and acid-addition salts thereof, at least one enzyme chosen from
2-electron oxidoreductases chosen from: pyranose oxidases, glucose oxidases, glycerol oxidases, lactate oxidases, pyruvate oxidases and uricases, and at least one donor for said at least one enzyme chosen from D-glucose, L-sorbose, D-xylose, glycerol, dihydroxyacetone, lactic acid and its salts; pyruvic acid and its salts; and uric acid and its salts.

32. A process for dyeing keratin fibers, comprising applying a ready-to-use composition for the oxidation dyeing of keratin fibers to said fibers and developing for a period sufficient to achieve a desired coloration, wherein said composition comprises:

at least one first oxidation base chosen from para-phenylenediamines and acid-addition salts thereof, at least one second oxidation base chosen from
para-aminophenol compounds chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof, at least one coupler chosen from 2-methyl-5-N-(β-hydroxyethyl)aminophenol and acid-addition salts thereof, at least one additional coupler other than 2-methyl-5-N-(β-hydroxyethyl)aminophenol, and acid-addition salts thereof, wherein said at least one additional coupler is chosen from meta-phenylenediamines, meta-aminophenols other than 2-methyl-5-N-(β-hydroxyethyl)aminophenol, meta-diphenols, heterocyclic couplers, and acid-addition salts thereof, at least one enzyme chosen from
2-electron oxidoreductases chosen from: pyranose oxidases, glucose oxidases, glycerol oxidases, lactate oxidases, pyruvate oxidases and uricases, and at least one donor for said at least one enzyme chosen from D-glucose, L-sorbose, D-xylose, glycerol, dihydroxyacetone, lactic acid and its salts; pyruvic acid and its salts; and uric acid and its salts.

33. A process for dyeing keratin fibers, comprising applying a composition for the oxidation dyeing of keratin fibers to said fibers and developing for a period sufficient to achieve a desired coloration, wherein said composition comprises:

para-phenylenediamine, para-aminophenol, 2-methyl-5-N-(β-hydroxyethyl)aminophenol, uricase, and uric acid.

34. A process for dyeing keratin fibers, comprising:

separately storing a first composition, separately storing a second composition, thereafter mixing said firs t a nd second compositions, applying said mixture to said fibers, and developing for a period sufficient to achieve a desired coloration, wherein said first composition comprises at least one first oxidation base chosen from para-phenylenediamines and acid-addition salts thereof, at least one second oxidation base chosen from para-aminophenols and acid-addition salts thereof, and at least one coupler chosen from 2-methyl-5-N-(β-hydroxyethyl)aminophenol and acid-addition salts thereof, and wherein said second composition comprises at least one enzyme chosen from 2-electro oxidoreductases and at least one donor for said at least one enzyme.

35. A process for dyeing keratin fibers, comprising:

separately storing a first composition, separately storing a second composition, thereafter mixing said first and second compositions,
applying said mixture to said fibers, and
developing for a period sufficient to achieve a desired coloration,
wherein said first composition comprises at least one first oxidation base chosen from para-phenylenediamines and acid-addition salts thereof,
at least one second oxidation base chosen from
para-aminophenol compounds chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof, and
at least one coupler chosen from 2-methyl-5-N-(β-hydroxyethyl)aminophenol and acid-addition salts thereof, and
wherein said second composition comprises at least one enzyme chosen from
2-electron oxidoreductases chosen from: pyranose oxidases, glucose oxidases, glycerol oxidases, lactate oxidases, pyruvate oxidases and uricases, and
at least one donor for said at least one enzyme, which is chosen from D-glucose, L-sorbose, D-xylose, glycerol, dihydroxyacetone, lactic acid and its salts; pyruvic acid and its salts; and uric acid and its salts.

36. A process for dyeing keratin fibers, comprising:
separately storing a first composition,
separately storing a second composition,
thereafter mixing said first and second compositions,
applying said mixture to said fibers, and
developing for a period sufficient to achieve a desired coloration,
wherein said first composition comprises para-phenylenediamine, para-aminophenol, and 2-methyl-5-N-(β-hydroxyethyl)aminophenol, and
wherein said second composition comprises uricase and uric acid.

37. A process for dyeing keratin fibers, comprising:
separately storing a first composition,
separately storing a second composition,
thereafter mixing said first and second compositions,
applying said mixture to said fibers, and
developing for a period sufficient to achieve a desired coloration,
wherein said first composition comprises at least one first oxidation base chosen from para-phenylenediamines and acid-addition salts thereof,
at least one second oxidation base chosen from
para-aminophenol compounds chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof, and
at least one coupler chosen from 2-methyl-5-N-(β-hydroxyethyl)aminophenol and acid-addition salts thereof, and
at least one additional coupler other than 2-methyl-5-N-(β-hydroxyethyl)aminophenol and acid-addition salts thereof, wherein said at least one additional coupler is chosen from meta-phenylenediamines, meta-aminophenols other than 2-methyl-5-N-(β-hydroxyethyl)aminophenol, meta-diphenols, heterocyclic couplers, and acid-addition salts thereof, and
wherein said second composition comprises at least one enzyme chosen from
2-electron oxidoreductases chosen from: pyranose oxidases, glucose oxidases, glycerol oxidases, lactate oxidases, pyruvate oxidases and uricases, and
at least one donor for said at least one enzyme, which is chosen from D-glucose, L-sorbose, D-xylose, glycerol, dihydroxyacetone, lactic acid and its salts; pyruvic acid and its salts; and uric acid and its salts.

38. A multi-compartment dyeing kit, comprising at least two separate compartments, wherein a first compartment contains a first composition and a second compartment contains a second composition,
wherein said first composition comprises at least one first oxidation base chosen from para-phenylenediamines and acid-addition salts thereof, at least one second oxidation base chosen from para-aminophenols and salts thereof, and at least one coupler chosen from 2-methyl-5-N-(β-hydroxyethyl)aminophenol and acid-addition salts thereof, and
wherein said second composition comprise at least one enzyme chosen from 2-electron oxidoreductases and at least one donor for said at least one enzyme.

39. A multi-compartment dyeing kit, comprising at least two separate compartments, wherein a first compartment contains a first composition and a second compartment contains a second composition,
wherein said first composition comprises at least one first oxidation base chosen from para-phenylenediamines and acid-addition salts thereof,
at least one second oxidation base chosen from
para-aminophenol compound s chosen from: para-aminophenol, 4-amino-3-methylphenol, 4-amino-3-fluorophenol, 4-amino-3-hydroxymethylphenol, 4-amino-2-methyl phenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof, and
at least one coupler chosen from 2-methyl-5-N-(β-hydroxyethyl)aminophenol and acid-addition salts thereof, and
wherein said second composition comprises at least one enzyme chosen from
2-electron oxido reductases chosen from: pyranose oxidases, glucose oxidases, glycerol oxidases, lactate oxidases, pyruvate oxidases and uricases, and
at least one donor for said at least one enzyme, which is chosen from D-glucose, L-sorbose, D-xylose, glycerol, dihydroxyacetone, lactic acid and its salts; pyruvic acid and its salts; and uric acid and its salts.

40. A multi-compartment dyeing kit, comprising at least two separate compartments, wherein a first compartment contains a first composition and a second compartment contains a second composition,
wherein said first composition comprises para-phenylenediamine, para-aminophenol, 2-methyl-5-N-(β-hydroxyethyl)aminophenol, and wherein said second composition comprises uricase and uric acid.

41. A multi-compartment dyeing kit, comprising at least two separate compartments, wherein a first compartment contains a first composition and a second compartment contains a second composition, wherein said first composition comprises at least one first oxidation base chosen from para-phenylenediamines and acid-addition salts thereof, at least one second oxidation base chosen from para-aminophenol compounds chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof, and at least one coupler chosen from 2-methyl-5-N-(β-hydroxyethyl)aminophenol and acid-addition salts thereof, at least one additional coupler other than 2-methyl-5-N-(β-hydroxyethyl)aminophenol, and acid-addition salts thereof, wherein said at least one additional coupler is chosen from meta-phenylenediamines, meta-aminophenols other than 2-methyl-5-N-(β-hydroxyethyl)aminophenol, meta-diphenols, heterocyclic couplers, and acid-addition salts thereof, and wherein said second composition comprises at least one enzyme chosen from 2-electron oxidoreductases chosen from: pyranose oxidases, glucose oxidases, glycerol oxidases, lactate oxidases, pyruvate oxidases and uricases, and at least one donor for said at least one enzyme, which is chosen from D-glucose, L-sorbose, D-xylose, glycerol, dihydroxyacetone, lactic acid and its salts; pyruvic acid and its salts; and uric and its salts.

* * * * *

UNITED STATES PATENT AND TRADEMARK OFFICE
CERTIFICATE OF CORRECTION

PATENT NO. : 6,840,966 B1
APPLICATION NO. : 10/645881
DATED : January 11, 2005
INVENTOR(S) : De La Mettrie et al.

It is certified that error appears in the above-identified patent and that said Letters Patent is hereby corrected as shown below:

On the Title Page, item (63), "Feb. 15, 2001" should read --June 30, 1999--.

Column 9, line 4, "meta-aminophenols," should read --meta-diphenols,--.

Column 10, line 50, "firs t a nd" should read --first and--.

Column 10, line 62, "2-electro" should read --2-electron--.

Column 12, line 28, "composition comprise" should read --composition comprises--.

Column 12, line 40, "compound s" should read --compounds--.

Column 12, line 54, "oxido reductases" should read --oxidoreductases--.

Column 14, line 18, after "uric", insert --acid--.

Signed and Sealed this

Twenty-seventh Day of February, 2007

JON W. DUDAS
*Director of the United States Patent and Trademark Office*